US010327814B2

(12) United States Patent
Miki

(10) Patent No.: US 10,327,814 B2
(45) Date of Patent: Jun. 25, 2019

(54) NAIL PLATE GROWTH GUIDE SURGICAL IMPLANTATION KIT

(71) Applicant: Roberto Augusto Miki, Pinecrest, FL (US)

(72) Inventor: Roberto Augusto Miki, Pinecrest, FL (US)

( * ) Notice: Subject to any disclaimer, the term of this patent is extended or adjusted under 35 U.S.C. 154(b) by 0 days.

(21) Appl. No.: 16/069,238

(22) PCT Filed: Jan. 18, 2017

(86) PCT No.: PCT/US2017/013922
§ 371 (c)(1),
(2) Date: Jul. 11, 2018

(87) PCT Pub. No.: WO2017/132024
PCT Pub. Date: Aug. 3, 2017

(65) Prior Publication Data
US 2019/0021766 A1   Jan. 24, 2019

Related U.S. Application Data

(60) Provisional application No. 62/288,821, filed on Jan. 29, 2016.

(51) Int. Cl.
*A61F 5/11* (2006.01)
*A61M 5/32* (2006.01)
(Continued)

(52) U.S. Cl.
CPC .......... *A61B 17/54* (2013.01); *A61B 17/0467* (2013.01); *A61B 17/062* (2013.01);
(Continued)

(58) Field of Classification Search
CPC ......... A61B 17/54; A61B 46/20; A61B 50/30; A61B 50/33; A61B 17/0467;
(Continued)

(56) References Cited

U.S. PATENT DOCUMENTS

| 4,559,055 A | 12/1985 | Ogunro |
| 4,819,623 A | 4/1989 | Ogunro |

(Continued)

FOREIGN PATENT DOCUMENTS

| WO | WO 2007/053849 A2 | 5/2007 |
| WO | WO 2014/076819 A1 | 3/2014 |

OTHER PUBLICATIONS

"Acute Nail Bed Injuries", Brown, RE. Hand Clinics. vol. 18, No. 4, 2002, pp. 561-576.

(Continued)

*Primary Examiner* — Chun Hoi Cheung
(74) *Attorney, Agent, or Firm* — Gordon & Jacobson, P.C.

(57) ABSTRACT

A surgical kit for the repair of a nail bed includes implantable nail plate guides adapted to guide the regrowth of a fingernail over a nail bed, drapes, a suture needle with absorbable suture, a suture needle with non-absorbable suture, wound dressings, and all instruments required to perform the procedure. The instruments preferably include an elevator, a needle driver, a clamp, a tweezers, and a scissors. The kit also includes anesthesia, a syringe, and needles for loading and then administering the anesthesia to the finger. The kit may include a tourniquet, antiseptic, and an antiinfective. Therefore, the kit assembles together several nail plate guides, the instruments for implanting a selected one of the nail plate guides onto the nail bed over a patient, the pre-implantation surgical preparation materials, and the post-implantation wound care materials.

18 Claims, 1 Drawing Sheet

(51) Int. Cl.
*A61B 17/00* (2006.01)
*A61B 17/04* (2006.01)
*A61B 17/06* (2006.01)
*A61B 17/30* (2006.01)
*A61B 17/32* (2006.01)
*A61B 17/54* (2006.01)
*A61B 46/20* (2016.01)
*A61B 50/30* (2016.01)
*A61B 50/33* (2016.01)
*A61F 13/06* (2006.01)
*A61F 13/10* (2006.01)
*A61M 19/00* (2006.01)
*A61B 17/062* (2006.01)
*A61B 17/132* (2006.01)
*A61B 17/3205* (2006.01)

(52) U.S. Cl.
CPC .. *A61B 17/06066* (2013.01); *A61B 17/06166* (2013.01); *A61B 17/1325* (2013.01); *A61B 17/30* (2013.01); *A61B 17/32* (2013.01); *A61B 17/3205* (2013.01); *A61B 46/20* (2016.02); *A61B 50/30* (2016.02); *A61B 50/33* (2016.02); *A61F 5/11* (2013.01); *A61F 13/068* (2013.01); *A61F 13/10* (2013.01); *A61F 13/105* (2013.01); *A61M 5/32* (2013.01); *A61M 5/329* (2013.01); *A61M 19/00* (2013.01); *A61B 2017/00004* (2013.01); *A61B 2017/305* (2013.01); *A61B 2017/320044* (2013.01); *A61B 2017/320052* (2013.01); *A61B 2046/201* (2016.02)

(58) Field of Classification Search
CPC ........ A61B 17/06066; A61B 17/06166; A61B 17/062; A61B 17/1325; A61B 17/30; A61B 17/32; A61B 17/3205; A61B 50/00; A61F 5/11; A61F 13/068; A61F 13/10; A61F 13/105; A61M 5/32; A61M 5/329; A61M 19/00
USPC .......................................... 206/223, 570, 572
See application file for complete search history.

(56) References Cited

U.S. PATENT DOCUMENTS

| | | |
|---|---|---|
| 5,060,678 A | 10/1991 | Bauman et al. |
| 5,350,060 A * | 9/1994 | Alpern ............ A61B 17/06133 206/380 |
| 2004/0173232 A1* | 9/2004 | Chang .................... A45D 31/00 132/73 |
| 2008/0276950 A1* | 11/2008 | Fracassi ................. A45C 11/00 132/73 |
| 2011/0276065 A1* | 11/2011 | Bauman ................. A45D 31/00 606/151 |
| 2013/0105337 A1* | 5/2013 | Williams ................ A61F 17/00 206/210 |
| 2016/0030368 A1* | 2/2016 | Atkins, Jr. ........... A61K 31/167 514/537 |
| 2018/0249943 A1* | 9/2018 | Moein .................. A61B 5/4331 |

OTHER PUBLICATIONS

"Nail Surgery: Practical Tips and Treatment Options", Jellinek, NJ. Dermatologic Therapy, vol. 20, 2007, pp. 68-74.

* cited by examiner

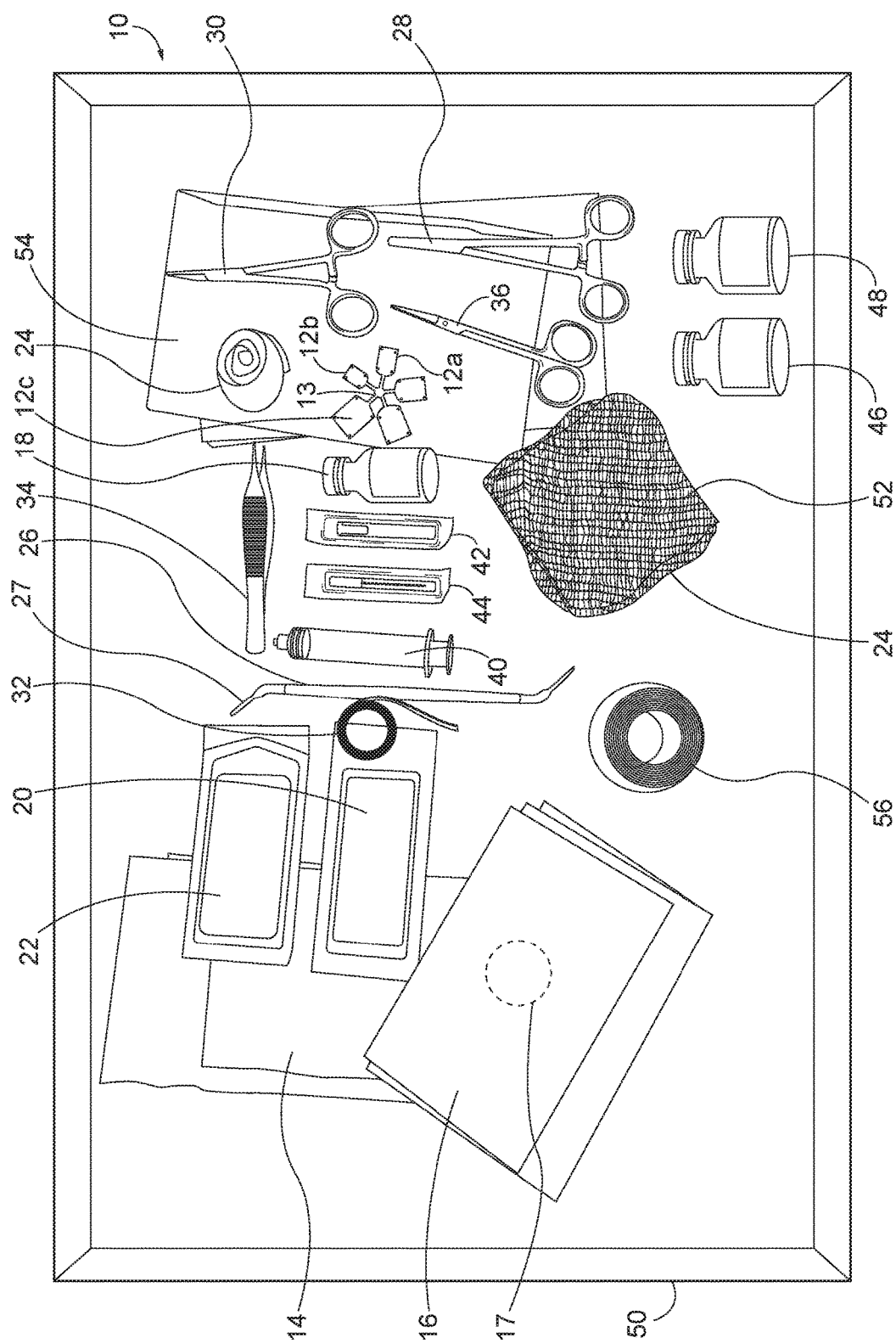

NAIL PLATE GROWTH GUIDE SURGICAL IMPLANTATION KIT

BACKGROUND OF THE INVENTION

1. Field of the Invention

The present invention generally relates to surgical repair of a human nail bed. More particularly, the present invention is directed to a surgical kit for the surgical repair of a human nail bed and facilitation of regrowth of a human nail along the nail bed.

2. State of the Art

When healthy, a nail plate at the tip of a digit (finger or toe) has the function of protecting the tip of the digit and the surrounding soft tissue from injuries. Further, the fingernail also serves to enhance the precise delicate movements of the distal end of the finger through counter-pressure exerted on the pulp of the finger.

It is not uncommon for an individual to lose a nail plate from one or more digits, due to trauma, disease, infection, etc. Typically replacement of the missing nail plate is accomplished by a regrowth of a new nail, which is normally a natural occurrence. However, problems associated with the normal regrowth of a missing nail may include, but are not limited to, the passage of the nail from the root or sinus area, through and beyond a skin portion disposed at the base of a corresponding nail bed. Specifically, the growth origin of a new nail is located under a skin portion located at the nails proximal end and under the epidermis, generally disposed adjacent the inner end or base of the nail bed.

As a result, it is important to replace missing nails in an efficient and effective manner. In understanding the normally natural procedure involved in the regrowth of a missing nail it is advantageous to understand at least the basic structural features or components of the nail.

The human nail comprises a nail plate, a nail matrix and a nail bed disposed below the nail plate and connected thereto. The matrix is actually part of the nail bed and is located there beneath and contains nerves, lymph and blood vessels. The nail matrix is responsible for producing cells that eventually become the nail plate. As the new nail plate cells are made, they push older nail plate cells forward. In this manner the older cells become compressed, flat and translucent.

The nail bed is the skin beneath the nail plate and like all skin is made up of two types of tissues including the dermis and the epidermis. The nail sinus is the zone or location associated with the nail root and underlies the base of the nail underneath the skin portion disposed at or substantially adjacent to the base of the nail plate. As indicated, the nail plate is the hard part of the nail made of translucent keratin protein. A free margin of or distal edge of the nail is the anterior margin of the nail plate corresponding to the abrasive or cutting edge of the nail.

It is commonly recognized that replacement of a missing nail is an important factor in maintaining an individual's health and the replacement thereof, through regrowth of a new nail, is important.

Therefore, systems have been for the regrowth of a missing nail. By way of example, U.S. Pat. No. 4,819,623 to Ogunro describes a thin plastic inert device that is intended to fit into the eponychial fold and over the nail bed to protect tissue during healing and provide a guide along which the healing nail bed can assume a smooth shape.

Such a proposed device is preferably capable of temporary attachment to the affected digit (finger or toe) in a manner that does not derogatorily affect use of the corresponding digit in the normal course of an individual's daily activities. The device is also structured, dimensioned and configured to protect at least the nail bed of the affected digit during the regrowth period, by being at least partially disposed in spaced, overlying and/or covering relation to the nail bed.

While these features are desirable, a nail plate guide corresponding to the teaching in Ogunro has not been adopted into widespread use.

SUMMARY OF THE INVENTION

In order to properly implant a nail plate guide a large number of instruments and materials from various locations within a surgical center are required. The inconvenience of collecting the instruments and materials needed for a relatively 'simple' and surgery may dissuade some practitioners from even undertaking the repair.

In accord with an invention described herein, a surgical kit is provided that assembles the various elements required for the repair of a nail bed: a plurality of pre-formed nail plate guides of various sizes, at least one surgical drape, anesthesia, at least one suture needle with absorbable suture, at least one suture needle with non-absorbable suture, wound dressings, and all instruments required to perform the procedure. The instruments preferably include a surgical elevator to separate (dissect) and remove the broken nail from the nail bed, a needle driver to advance the suture needles through the tissue and the nail plate guide, a clamp, e.g., to secure a tourniquet, a tweezers, e.g., to pickup and manipulate suture needles and wound debris, and a scissors, e.g., to cut suture. Also, the kit includes a syringe and preferably two different gauge needles for loading and then administering the anesthesia to the finger. Additionally, the kit may include a tourniquet. Also, the kit may include an antiseptic and an antiinfective. The elements of the kit are assembled in a tray or box, with the contents preferably sterilized and ready for surgical use.

When a patient has suffered an injury to the nail bed, such as by laceration through the bed or a crushed finger that compromises the nail bed, surgical repair is appropriate. The provided kit assembles several nail plate guide implants of different sizes, the instruments for implanting a selected one of the nail plate guides onto the nail bed over a patient, the pre-implantation surgical preparation materials, and the post-implantation wound care materials, all in one sterilized kit. As such, the kit greatly facilitates the repair of a damaged nail bed.

BRIEF DESCRIPTION OF THE DRAWING

The FIGURE shows a surgical kit for the repair of a nail bed.

DETAILED DESCRIPTION OF THE PREFERRED EMBODIMENTS

Referring to the FIGURE, a surgical kit 10 for the repair of a damaged nail bed is shown. The surgical kit 10 assembles the various elements required for the repair of a nail bed: a plurality of pre-formed nail plate guides 12a, 12b, 12c of various sizes, one or more surgical drapes 14, 16, at least one suture needle with absorbable suture 20, at least one suture needle with non-absorbable suture 22, wound dressings 24, and all instruments required to perform the procedure. The instruments preferably include an elevator (e.g., a Freer elevator) 26 to separate (dissect) and remove the broken nail from the nail bed, a needle driver 28 to advance the suture needles 20, 22 through the tissue and the nail plate guides 12a, 12b, 12c, a clamp 30, e.g., to secure an optional tourniquet 32, a tweezers 34, e.g., to pickup and manipulate suture needles and wound debris, and a scissors 36, e.g., to cut suture. The kit 10 also includes a container of local anesthesia 18, a syringe 40, and preferably two different gauge needles 42, 44 for loading and then administering the anesthesia 18 to the finger. Additionally, the kit 10 may include antiseptic 46 and/or an antiinfective 48. The elements of the kit are assembled in a tray or box 50, with the contents preferably sterilized (or sterilizable within) and, as sterilized, ready for surgical use.

When a patient has suffered an injury to the nail bed, such as by laceration through the bed or a crushed finger that compromises the nail bed, surgical repair is appropriate. The kit 10 is preferably used as follows in performing the surgical repair.

The sealed sterilized kit 10 is brought intact into the operating room. The finger including the injured nail bed is prepped with the antiseptic 46. By way of example, the finger is swabbed with alcohol 46 using a gauze wipe.

The local anesthesia 18, such as lidocaine (or other aminoamide or aminoester local anesthetics), is acquired from the kit. The syringe 40 is coupled to the larger needle 42, such as an 18-gauge needle. The larger needle 42 is inserted into the containerized anesthesia 18 and drawn into the syringe 40. Then the larger needle 42 is removed from the syringe 40, and the smaller needle 44, such as a 25-gauge needle, is coupled to the syringe 40 for administration to the patient. The anesthesia 18 is injected with the syringe at the proximal joint of the finger on the volar side (metacarpal phalangeal joint), and numbness is thereby caused to set throughout the finger.

Once the anesthesia 18 has taken effect, the finger is wiped with the topical antiinfective 48. A preferred antiinfective is povidone-iodine (PVP-I), also commonly referred to under the brand name Betadine.

The finger is then draped. The kit preferably provides two different types of drapes 14, 16. The first drape 14, formed as an integral sheet (no openings) is placed under the finger as a sterilized barrier over the operating table. The second drape 16 is formed with a hole 17 in a central portion thereof. The subject finger is positioned through the hole 17 in the second drape and exposed on top of the second drape, with the remainder of the hand sandwiched between the first and second drapes 14, 16. Other draping options may be used, including a unitary drape for placement both under the finger and over the remaining portion of the hand.

The tourniquet 32 is then cinched about the base of the finger, with circumferential pressure retained to limit and/or prevent blood flow to the finger. The tourniquet 32 is preferably a length of elastic material (or even a portion or entirety of an elastic glove). The tourniquet 32 may be tied, or releasably secured with the clamp 30 from the kit 10.

The elevator 26 from the kit is then used to separate and elevate any remaining nail from the nail bed, and provide the nail bed in an exposed state. The elevator 26 includes an end 27 with a relatively flat and blunt surface adapted to separate (dissect) tissue without causing significant trauma to the tissue. The damage to the nail bed is then assessed by the surgeon. The nail bed is irrigated and any foreign material and blood are removed. The tweezers 34 may be used for this end. The nail bed is again examined.

The suture needle with absorbable suture 20 is obtained from the kit. Using the needle driver 28, the needle and suture 20 are advanced about the wound to repair the nail bed, as necessary. Remaining suture is cut with the scissors 36.

The nail plate guides 12a, 12b, 12c are obtained from the kit and inspected and compared to the injured nail bed to determine the appropriate size one of the guides for the subject nail bed. The plurality of the nail plate guides 12a, 12b, 12c may be provided together, e.g., frangibly coupled about a common plastic armature 13. The appropriately sized guide 12a is removed from the armature 13. Each nail plate guide is preferably made from an inert polymer and has a curvature that approximates the natural curve of a healthy nail bed. Guide 12a is positioned over and onto the nail bed, but under the eponychial fold (cuticle).

The suture needle with non-absorbable suture 22 is used to secure the nail plate guide 12a directly to the tissue. At the conclusion of the procedure, the repaired finger is wrapped in a protective wound dressing. Wound dressing materials preferably provided in the kit include regular and non-stick gauze pad(s) 52, stretch conforming gauze roll(s) 54, such as Kling Conforming Bandage from Johnson & Johnson, and/or high elastic compress cohesive bandage(s) 56 having a combination of a rubber reinforced woven yarns and a latex coating which allows cohesive properties, such as CoBand Wrap from 3M Nexcare.

The provided kit positions several nail plate guide implants of different sizes, the instruments for implanting the implant into a patient, the pre-implantation surgical preparation materials, and the post-implantation wound care materials all in one sterilized kit. As such, the kit greatly facilitates the repair of a damaged nail bed.

Once the finger is permitted to heal, the new nail will grow between the nail bed and the nail plate guide, ensuring that the new nail is properly formed. Once the nail has sufficiently grown back, the surgeon can release the non-absorbable sutures and remove the implanted nail plate guide. However, such guide should be substantially loosened from the finger tissue by the intervening anatomical nail. The nail plate guide may release on its own once the nail grows back, such that a return trip to the surgeon specifically for nail plate guide removal is not required.

There have been described and illustrated herein embodiments of a surgical kit for the repair of a nail bed, and a method of such repair. While particular embodiments of the invention have been described, it is not intended that the invention be limited thereto, as it is intended that the invention be as broad in scope as the art will allow and that the specification be read likewise. Also, while the surgical kit described herein has primarily been described for use in repair of a fingernail associated with a finger of a human, the surgical kit may equally apply to appropriate surgical repair of a toenail, albeit with nail plate growth guides of appropriate sizes therefor. It will therefore be appreciated by those skilled in the art that yet other modifications could be made to the provided invention without deviating from its scope as claimed.

What is claimed is:
1. A surgical kit for the repair of a nail bed on a human digit to aid in regrowth of a nail on the digit, comprises:
   a) a plurality of pre-formed nail plate guides of various sizes;
   b) at least one surgical drape;
   c) a local anesthetic;

d) a syringe and at least one hollow needle for loading the anesthetic and then administering the anesthetic to numb the human digit;
e) an elevator instrument having a flat, blunt end adapted to separate a broken nail on the digit from the nail bed;
f) a plurality of suture needles with suture;
g) wound dressings,
   wherein all elements of the kit are assembled together in a container.

2. The surgical kit of claim 1, wherein the plurality of nail plate guides are frangibly coupled together on a plastic armature.

3. The surgical kit of claim 1, wherein the plurality of suture needles with suture includes,
   at least one suture needle with absorbable suture, and
   at least one suture needle with non-absorbable suture.

4. The surgical kit of claim 1, further comprising:
   an elastic tourniquet for the human digit.

5. The surgical kit of claim 4, further comprising:
   a clamp to temporarily secure the tourniquet about the human digit.

6. The surgical kit of claim 1, wherein the local anesthetic is lidocaine.

7. The surgical kit of claim 1, wherein the at least one hollow needle includes at least two needles of different gauges.

8. The surgical kit of claim 7, wherein a larger hollow needle is an 18-gauge needle, and a smaller hollow needle is a 25-gauge needle.

9. The surgical kit of claim 1, further comprising an antiseptic.

10. The surgical kit of claim 9, further comprising an anti-infective that is different from the antiseptic.

11. The surgical kit of claim 10, wherein the antiseptic is alcohol, and the anti-infective is povidone-iodine.

12. The surgical kit of claim 1, wherein the at least one surgical drape includes a first drape having an integral surface within its outer borders, and a second drape having a hole in a central portion thereof.

13. The surgical kit of claim 1, wherein the wound dressing includes a plurality of at least one gauze pad, a stretch conforming gauze roll, and a high elastic compress cohesive bandage.

14. The surgical kit of claim 1, further comprising:
   a needle driver to advance the suture needles through tissue on the human digit and one of the nail plate guides;
   a tweezers; and
   a scissors.

15. The surgical kit of claim 1, wherein all elements in the container are sterilized.

16. A surgical kit for the repair of a nail bed on a human digit to aid in regrowth of a nail on the digit, comprises:
   a) a plurality of pre-formed nail plate guides of various sizes;
   b) at least one surgical drape;
   c) a container of local anesthetic;
   d) a syringe;
   e) a first hollow needle of a first gauge for loading the anesthetic from the container into the syringe;
   f) a second hollow needle of a second gauge different than the first gauge for administering the anesthetic from the syringe to the human digit;
   g) an elevator instrument having a flat, blunt end adapted to separate a broken nail on the human digit from the nail bed;
   h) at least one suture needle with absorbable suture;
   i) at least one suture needle with non-absorbable suture;
   j) an elastic tourniquet for the human digit;
   k) an antiseptic; and
   l) wound dressings,
      wherein all elements of the kit are assembled together in a container.

17. A surgical kit according to claim 16, further comprising:
   a needle driver to advance the suture needles through tissue on the human digit and one of the nail plate guides;
   a tweezers; and
   a scissors.

18. A surgical kit for the repair of a nail bed on a human digit to aid in regrowth of a nail on the digit, consisting of:
   a) a plurality of pre-formed nail plate guides of various sizes;
   b) at least one surgical drape;
   c) a container of local anesthetic;
   d) a syringe and at least one hollow needle for loading the anesthetic and then administering the anesthetic to numb the human digit;
   e) an elevator instrument having a flat, blunt end adapted to separate a broken nail on the human digit from the nail bed;
   f) at least one suture needle with suture;
   g) an elastic tourniquet for the human digit;
   h) at least one of an antiseptic and an anti-infective;
   i) at least one wound dressing;
   g) a needle driver to advance the suture needles through tissue on the human digit and one of the nail plate guides;
   j) a tweezers; and
   k) a scissors,
      wherein all elements of the kit are assembled together in a container.

* * * * *